US00PP25131P3

(12) United States Plant Patent
Sheehan

(10) Patent No.: US PP25,131 P3
(45) Date of Patent: Dec. 2, 2014

(54) GRAPEVINE NAMED 'SHEEGENE-16'

(50) Latin Name: *Vitis vinifera*
Varietal Denomination: Sheegene-16

(75) Inventor: Timothy P. Sheehan, Vancouver, WA (US)

(73) Assignee: Sheehan Genetics, LLC, Fresno, CA (US)

( * ) Notice: Subject to any disclaimer, the term of this patent is extended or adjusted under 35 U.S.C. 154(b) by 0 days.

(21) Appl. No.: 13/506,258

(22) Filed: Apr. 6, 2012

(65) Prior Publication Data

US 2013/0269071 P1 Oct. 10, 2013

(51) Int. Cl.
*A01H 5/00* (2006.01)

(52) U.S. Cl.
USPC ..... Plt./205

(58) Field of Classification Search
USPC ..... Plt./205, 206
See application file for complete search history.

*Primary Examiner* — Anne Grunberg
(74) *Attorney, Agent, or Firm* — Baker Manock & Jensen, PC; Eric C. Cole

(57) ABSTRACT

A new and distinct variety of grapevine characterized by the production of large, red-colored seeded grapes that mature in early September, approximately six to eight weeks later than 'Flame Seedless' (unpatented) when grown in the San Joaquin Valley of Central California. The grapes of this new variety are produced on strong woody stems and branches and are well adapted to commercial handling.

1 Drawing Sheet

Latin name of the genius and species of the plant claimed: The claimed plant relates to a new and distinct variety of *Vitis vinifera* to be known as 'Sheegene-16'.

Variety denomination: The new variety of *Vitis vinifera* is the result of hybridization of 'R5V38-44' (unpatented), the pollen parent, and 'Red Globe' (U.S. Plant Pat. No. 4,787), the seed parent. The new variety was first hybridized by Timothy P. Sheehan in the Spring of 2000. The new variety was asexually propagated in the dormant season of 2003, grafted on virus-free rootstock in a *Vitis vinifera* variety block located East of Fowler, Calif. The new variety was planted as rooted cuttings in June of 2007 in a *Vitis vinifera* variety block located northwest of Delano, Calif. The new variety produces a large, red-colored seeded grape with very good flavor. The new variety has been shown to maintain its distinguishing characteristics through asexual propagation.

The new variety is distinguished from its pollen parent, 'R5V38-44' (unpatented), in that the new variety produces red-colored seeded grapes, as compared to the black-colored seedless grapes produced by its pollen parent, 'R5V38-44' (unpatented). The new variety is distinguished from its seed parent, 'Red Globe'(U.S. Plant Pat. No. 4,787), in that the new variety produces large sized red-colored seeded grapes, as compared to its seed parent, 'Red Globe' (U.S. Plant Pat. No. 4,787), that produces exceptionally large red-colored seeded grapes.

CROSS REFERENCE TO RELATED APPLICATIONS

The claimed plant is not subject of a related application.

STATEMENT OF ANY FEDERALLY-SPONSORED RESEARCH AND DEVELOPMENT

The claimed plant is not subject of Federally-sponsored research or development.

BACKGROUND OF THE INVENTION

The present invention relates to a new and distinct variety of grapevine that produces a large, red-colored seeded grape that matures during early September when grown in the San Joaquin Valley of Central California.

SUMMARY OF THE INVENTION

The 'Sheegene-16' grapevine is characterized by producing a large, red-colored seeded grape that has very good flavor and it is productive and mature for harvesting and shipment in early September when grown in the San Joaquin Valley of Central California. The new variety can be compared to 'Flame Seedless' (unpatented) but the grapes produced by the new variety mature approximately six to eight weeks later, among other distinguishing characteristics.

BRIEF DESCRIPTION OF THE DRAWINGS

The accompanying drawing is a color photograph that shows a branch displaying nodes along the top portion of the photograph, a cluster of mature grapes is located directly below with several immature leaves shown to the right of the cluster, directly below the immature leaves is a mature leaf and an immature leaf, two small clusters of mature grapes and four grapes cut in half displaying the color of the flesh and the shape of the berries are shown in lower-left center of the photograph, and at the bottom of the photograph is an immature branch displaying leaves and tendrils.

DETAILED BOTANICAL DESCRIPTION

Referring more to the horticultural description of the new and distinct variety of grapevine, the following has been observed under the ecological conditions prevailing at the origin vineyard located near Delano, Calif., in the San Joaquin Valley of Central California. All major color descriptions are by reference to the Dictionary of Color by Maerz & Paul, First Edition, published in 1930. Common colors names are also used in several instances.

Vine:

*Size*.—Medium to large.
*Vigor*.—Very good.
*Chilling requirements*.—Normal for grapevines in the lower San Joaquin Valley of Central California.
*Figure*.—With wide cordons forming a "T" shape.
*Productive capacity*.—Very good.
*Regularity of bearing*.—Regular.

Trunk:

*Size*.—Medium to large; 2 inches [5.08 cm] in circumference, 2.4 inches [6.10 cm] above ground (5 year old wood).
*Surface texture*.—Rough, shaggy.
*Color of bark*.—P1.7 H1 Casserole Rosite Gingerspice Eskimo+(5 year old wood).
*Mature cane color*.—P1.7 H9 Liver Brown Autumn Oak — (8 to 12 month old wood).
*Nodes*.—Eight nodes on cane, cane is 21 inches [53.34 cm] long.
*Length between nodes*.—3½ to 6 inches [8.89 to 15.24 cm].
*Shoot length*.—6 inches [15.24 cm].
*Shoot shape*.—Slender.
*Shoot habit*.—Droopy.
*Tendrils number/location*.—Single at node.
*Tendrils length*.—2⅞ inches [7.30 cm].
*Tendrils form*.—Bifurcate.
*Bud shape*.—Triangular.
*Bud size*.—Small; 0.078 inches [2 mm].

Branches:

*Size*.—Medium.
*Cordons*.—25 inches (63.50 cm) on one side of trunk ; 22½ inches (57.15 cm) on the other side of trunk.
*Surface texture*.—Rough.
*Color* (*one year or older branches*).—P1.6 L5 Corinthian Pr.
*Color* (*immature branches*).—P1.5 G4 Blush Rose (Upper side); P1.19 E6 Calliste Green (Lower side).

Leaves:

*Size*.—Large.
*Density*.—Dense.
*Average length*.—5½ to 7 inches [13.97 to 17.78 cm].
*Average width*.—4½ to 8 inches [11.43 to 20.32 cm].
*Form*.—Pentagonal.
*Texture* (*upper surface*).—Smooth.
*Texture* (*lower surface*).—Slightly glabrous.
*Leaf vein color*.—P1.20 K1 Russet gr.
*Margin form*.—Undulate.
*Leaf margin*.—Toothed.
*Leaf vein thickness*.—0.08 inches [2 mm].
*Stem glands*.—None.
*Petiole size*.—Moderate.
*Petiole length*.—3 inches [7.62 cm].
*Petiole color* (*lower surface*.—P1.9 H7 Liverbrown+ Autumn Oak.
*Petiole color* (*upper surface*).—P1.17 L7 Viridine y.
*Leaf sinus form*.—Upside down "U" shape.
*Lobes* (*average*).—Five.
*Stipules*.—None.
*Tooth size*.—0.20 to 0.31 inches [5 to 8 mm] in width; 0.28 to 0.31 inches [7 to 8 mm] in length.
*Tooth number*.—10 to 20 per lobe.

Inflorescence:

*Size*.—5.51 to 6.69 inches [14 to 17 cm] in length.
*Number per spur*.—One to two.
*Number per vine*.—Many; up to fifty-two clusters.

Flowers:

*Flower buds*.—0.04 to 0.08 inches [1 to 2 mm] in length.
*Flower buds surface*.—Glabrous.
*Flower buds*.—Generally heavy.
*Date of bloom*.—May 7.
*Date of full bloom*.—May 12 to 14.
*Size* (*average*).—0.20 inches [5 mm].
*Petals* (*color*).—P1.7 C8 Mauve Taupe.
*Petals* (*size*).—0.16 inches [4 mm].
*Pistil color*.—P1.17 L8 Nova gr.
*Date of visible berry set*.—May 12 to 14.
*Size of berries*.—0.08 inches [ 2 mm] when fruit first set.

Fruit:

*Solids*.—18.2 Brix.
*Acids*.—0.34.
*Sugar/acid ratio*.—53.5.
*Juice pH*.—3.97.
*Seeds* (*number*).—One to two.
*Capstem pedicel*.—0.47 to 0.98 inches [12 to 25 mm].
*Berry weight*.—53.9 grams (1.90 oz).
*Juice color*.—P1.7 J8 Dominge.
*Cluster size*.—Large.
*Cluster density*.—Compact.
*Cluster average length* (*not including stem*).—6.50 inches [16.51 cm].
*Cluster average diameter*.—6.50 inches [16.51 cm].
*Cluster average weight*.—1.19 lb. [539.13 grams].
*Compactness*.—Compact.
*Cluster form*.—Conical.
*Stem*.—Generally large.
*Stem caliper*.—3.5 inches [8.89 cm].
*Berry size*.—Large.
*Berry form*.—Ovate.
*Berry numbers* (*average*).—90 berries per bunch.
*Berry size* (*average dimension along longitudinal axis*).—0.98 inches [2.49 cm].
*Berry size* (*average dimension along transverse axis*).—0.53 inches [1.35 cm].

Skin:

*Skin thickness*.—Medium.
*Texture*.—Semi-tough.
*Blush color*.—P1.18 L6 Love Bird.
*Ground color*.—P1.56 L12 Port Wine.
*Lenticels*.—None.

Flesh:

*Flesh color*.—P1.18 L6 Love Bird.
*Juice production*.—Good.
*Flavor*.—Very good.
*Aroma*.—Mild.
*Texture*.—Firm.
*Ripening*.—Even.
*Eating quality*.—Very good.
*Resistance to disease*.—Unknown.
*Harvesting*.—Early September in the San Joaquin Valley of Central California.
*Shipping and handling qualities*.—Very good.

Having thus described and illustrated our new variety of grapevine, we claim:

1. A new and distinct variety of grapevine, substantially as described and illustrated herein, characterized principally by its production of large, red-colored seeded grapes that mature six to eight weeks later in the season of ripening than 'Flame Seedless' (unpatented) which it resembles.

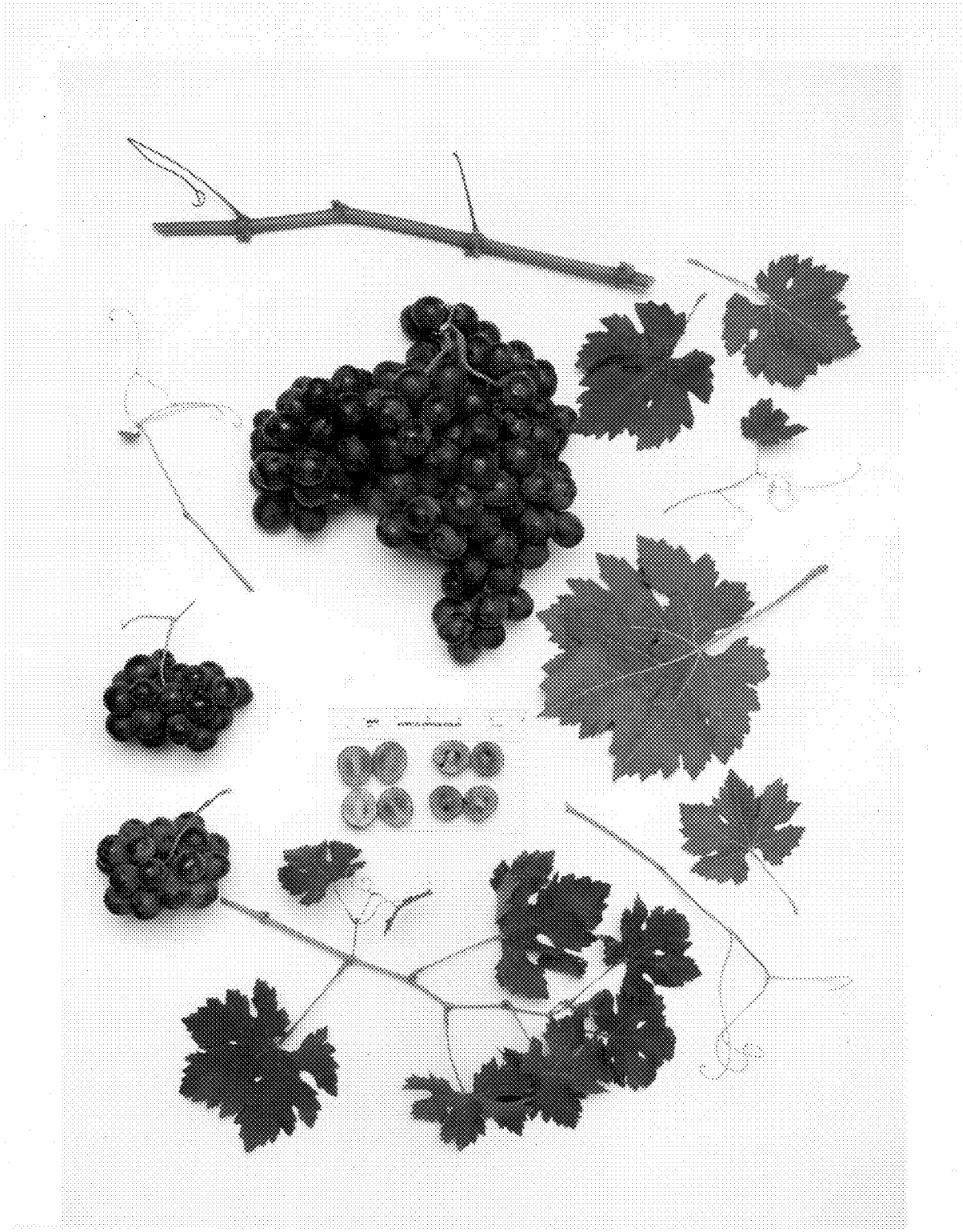

* * * * *